United States Patent
Nakasuga et al.

(10) Patent No.: US 11,078,209 B2
(45) Date of Patent: Aug. 3, 2021

(54) POLYCYCLIC AROMATIC HYDROCARBON DERIVATIVE, FLUORESCENT MATERIAL, PHOSPHORESCENT MATERIAL, AND LIGHT-MODULATING MATERIAL

(71) Applicants: SEKISUI CHEMICAL CO., LTD., Osaka (JP); HIROSHIMA UNIVERSITY, Higashihiroshima (JP)

(72) Inventors: Akira Nakasuga, Osaka (JP); Shoji Nozato, Osaka (JP); Hiroji Fukui, Osaka (JP); Takeharu Haino, Higashihiroshima (JP); Ryo Sekiya, Higashihiroshima (JP)

(73) Assignees: SEKISUI CHEMICAL CO., LTD., Osaka (JP); HIROSHIMA UNIVERSITY, Hiroshima (JP)

( * ) Notice: Subject to any disclaimer, the term of this patent is extended or adjusted under 35 U.S.C. 154(b) by 0 days.

(21) Appl. No.: 16/631,427

(22) PCT Filed: Jul. 17, 2018

(86) PCT No.: PCT/JP2018/026638
§ 371 (c)(1),
(2) Date: Jan. 15, 2020

(87) PCT Pub. No.: WO2019/017314
PCT Pub. Date: Jan. 24, 2019

(65) Prior Publication Data
US 2020/0207777 A1    Jul. 2, 2020

(30) Foreign Application Priority Data

Jul. 21, 2017 (JP) .............................. JP2017-141582

(51) Int. Cl.
C07D 487/22 (2006.01)
C07D 495/22 (2006.01)
C09K 11/06 (2006.01)

(52) U.S. Cl.
CPC ......... *C07D 487/22* (2013.01); *C07D 495/22* (2013.01); *C09K 11/06* (2013.01); *C09K 2211/1018* (2013.01)

(58) Field of Classification Search
CPC .... C07D 487/22; C07D 495/22; C09K 11/06; C09K 2211/1018; C09K 9/02; G02F 1/15
See application file for complete search history.

(56) References Cited

U.S. PATENT DOCUMENTS

| | | |
|---|---|---|
| 2009/0080056 A1 | 3/2009 | Yahara et al. |
| 2014/0134521 A1 | 5/2014 | Naito et al. |
| 2019/0292444 A1 | 9/2019 | Sun et al. |

FOREIGN PATENT DOCUMENTS

| | | |
|---|---|---|
| JP | 4-288550 A | 10/1992 |
| JP | 5-179237 A | 7/1993 |
| JP | 5-214334 A | 8/1993 |
| JP | 2008-153047 A | 7/2008 |
| JP | 2014-114205 A | 6/2014 |
| JP | 2016-207812 A | 12/2016 |
| JP | 2017-92210 A | 5/2017 |
| WO | WO-2007/061061 A1 | 5/2007 |
| WO | WO-2018/016616 A1 | 1/2018 |

OTHER PUBLICATIONS

Korshak, etal, Polybenzazoles containing 2-benzimidazolyl side groups, Macromolecules, 7(5), 589-98 (1974). (Year: 1974).*
Meng, et al, Colored Poly(arylene ether)s Containing Benzoylenebenzimidazole, Phthaloperinone, and Phthalocyanine Moieties, Macromolecules, 33(25), 9185-9191 (2000). (Year: 2000).*
El-Khouly, et al, Annulation of Tetrathiafulvalene to the Bay Region of Perylenediimide: Fast Electron-Transfer Processes in Polar and Nonpolar Solvents, Journal of Physical Chemistry C, 115(16), 8325-8334 (2011). (Year: 2011).*
Mamada, et al, Benzimidazole Derivatives: Synthesis, Physical Properties, and n-Type Semiconducting Properties, Chemistry—A European Journal, 20(37), 11835-11846 (2014). (Year: 2014).*
Warde, et al, DFT Studies of the Photophysical Properties of Fluorescent and Semiconductor Polycyclic Benzimidazole Derivatives, Journal of Fluorescence, 25(3), 685-694 (2015). (Year: 2015).*
Sakai, et al, Protonation-induced red-coloured circularly polarized luminescence of [5]carbohelicene fused by benzimidazole, Organic & Biomolecular Chemistry, 14(28), 6738-6743 (2016). (Year: 2016).*
Written Opinion of the International Searching Authority (PCT/ISA/237) for Application No. PCT/JP2018/026638 dated Oct. 2, 2018 (English Translation mailed Jan. 30, 2020).

(Continued)

*Primary Examiner* — Erich A Leeser
(74) *Attorney, Agent, or Firm* — Cheng Law Group, PLLC

(57) ABSTRACT

Provided is a new polycyclic aromatic hydrocarbon derivative. The polycyclic aromatic hydrocarbon derivative is a derivative of a polycyclic aromatic hydrocarbon having 6 or more aromatic rings and has a substituent represented by the following formula (1). (In the formula (1), $R_1$ and $R_2$ are carbon atoms of the aromatic rings in the polycyclic aromatic hydrocarbon, and $R_3$ to $R_5$ are carbon atoms of an aromatic ring or a heterocyclic ring in a group having the aromatic ring or the heterocyclic ring. n is 0 or 1, and m is the number of substituents.)

[Chemical 1]

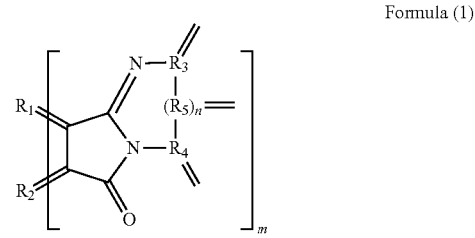

Formula (1)

3 Claims, 9 Drawing Sheets

(56) References Cited

OTHER PUBLICATIONS

Ai, Wei et al., "One-pot, aqueous-phase synthesis of graphene oxide functionalized with heterocyclic groups to give increased solubility in organic solvents", The Royal Society of Chemistry-RSC Advances, 2013, vol. 3, pp. 45-49.
Chang, Dong Wook et al., "Nitrogen-Doped Graphene Nanoplatelets from Simple Solution Edge-Functionalization of n-Type Field-Effect Transistors", Journal of the American Chemical Society, 2013, vol. 135, pp. 8981-8988.
Eng, Alex Yong et al., "Facile labelling of graphene oxide for superior capacitive energy storage and fluorescence applications", Physical Chemistry Chemical Physics—An international journal, 2016, vol. 18, pp. 9673-9681.
Haino, Takeharu et al., "Synthesis of Fluorescent Graphene Quantum Dots", Polymer Reprints, 2016, vol. 65, No. 2, ROMBUN No. 1R05, 4 pages.
Lu, Yanhong et al., "Synthesis and supercapacitor performance studies of N-doped graphene materials using o-phenylenediamine as the double-N precursor", Carbon, 2013, vol. 63, pp. 508-516.
Luan, Van Hoang et al., "The molecular level control of three-dimensional graphene oxide hydrogel structure by using various diamines", Chemical Engineering Journal, 2014, vol. 246, pp. 64-70.
Qi, Bao-Ping et al., "An efficient edge-functionalization method to tune the photoluminescence of graphene quantum dots", Nanoscale, 2015, vol. 7, pp. 5969-5973.
International Search Report for the Application No. PCT/JP2018/026638 dated Oct. 2, 2018.
Written Opinion of the International Searching Authority (PCT/ISA/237) for Application No. PCT/JP2018/026638 dated Oct. 2, 2018.
Dilthey, W. et al., "Maleinsäureaddukte an Phencyclon, [Heteropolare, XXVIII]", Journal für praktische Chemie, 1937, pp. 53-71.
Ji, Yuxing et al., "Electrochemical and electrochromic behaviors of polyaniline-graphene oxide composites on the glass substrate/Ag nano-film electrodes prepared by vertical target pulsed laser deposition", Dyes and Pigments, 2015, vol. 117, pp. 72-82.
Langhals, Heinz et al., "Angular Benzoperylenetetracarboxylic Bisimides", Chemistry—A European Journal, 2012, vol. 18, No. 41, pp. 13188-13194.
Langhals, Heinz et al., "Novel Fluorescent Dyes by the Extension of the Core of Perylenetetracarboxylic Bisimides", European Journal of Organic Chemistry, 2000, vol. 2000, No. 2, pp. 365-380.
Supplementary European Search Report for the Application No. EP 18 834 559.9 dated Feb. 3, 2021.

* cited by examiner

[FIG. 1]
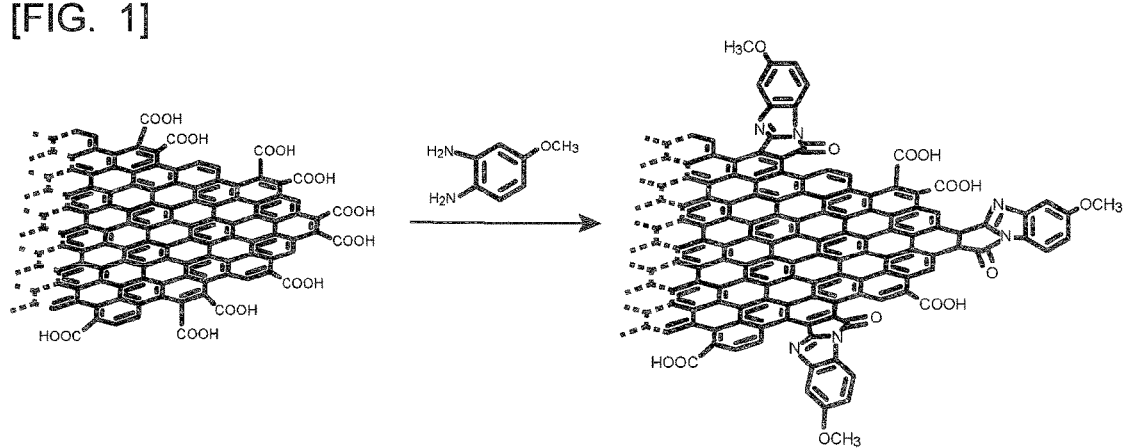
[FIG. 2]
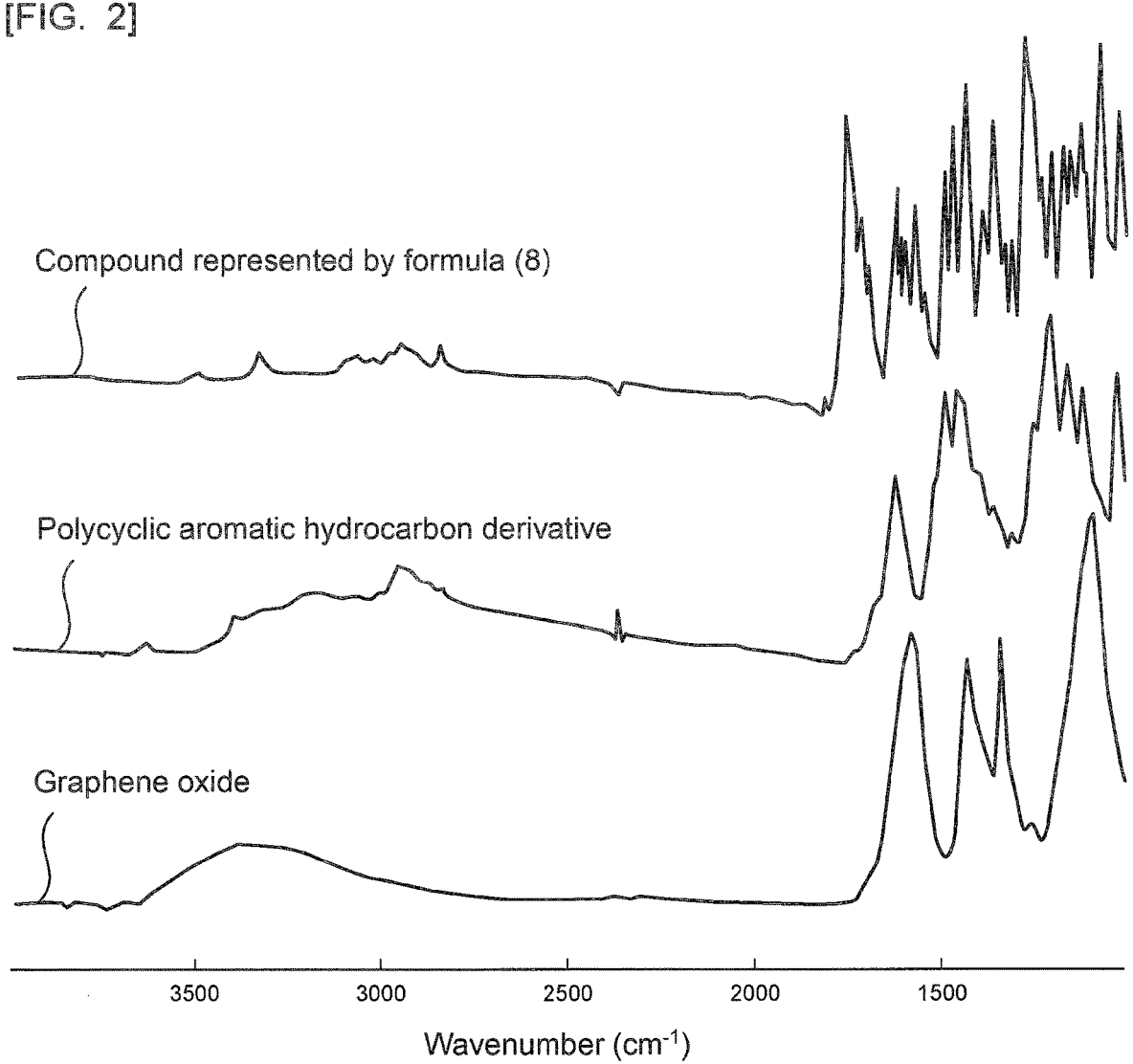

[FIG. 3]
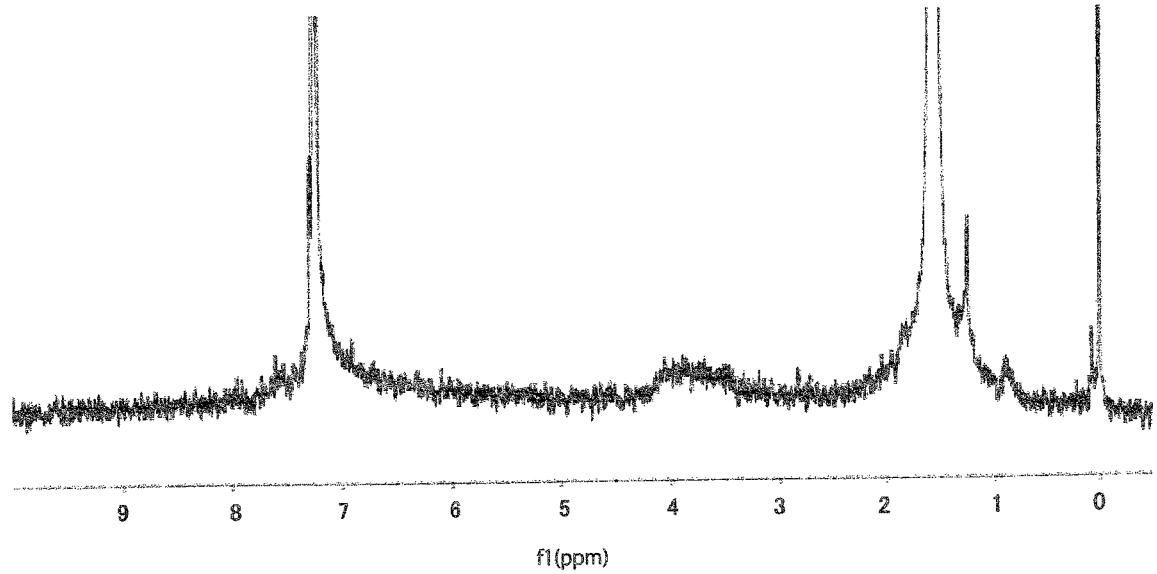
[FIG. 4]
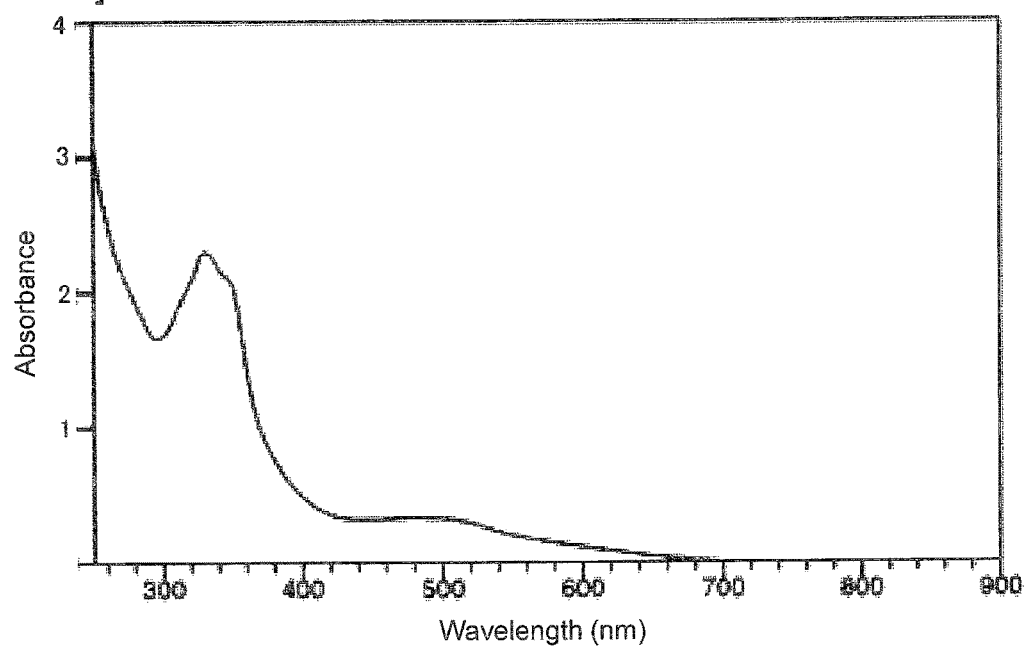

[FIG. 5]
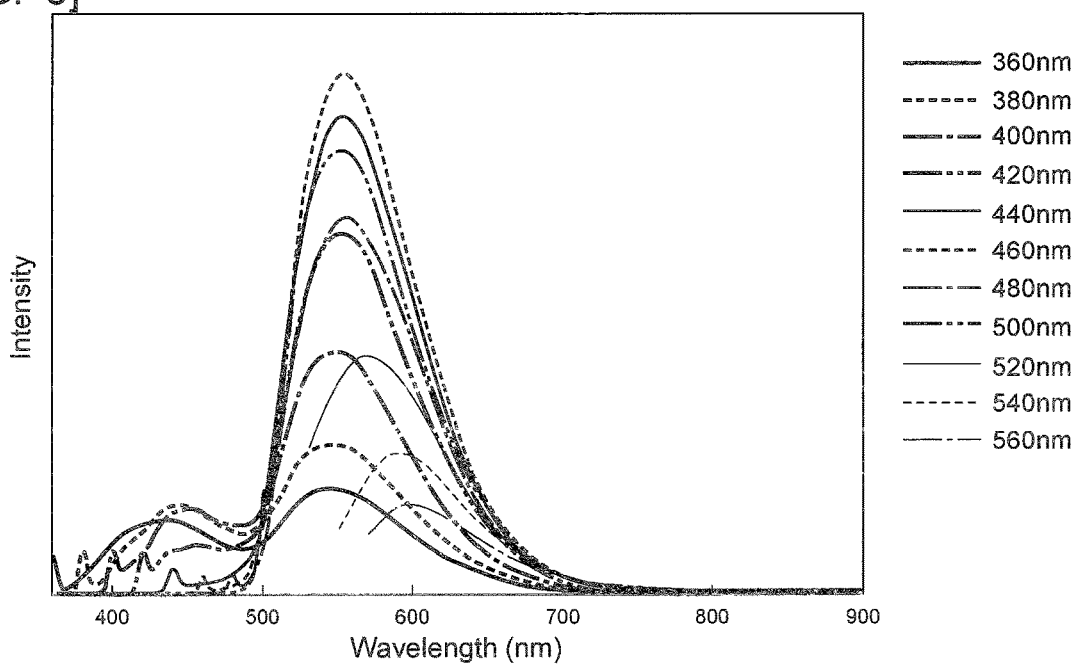
[FIG. 6]
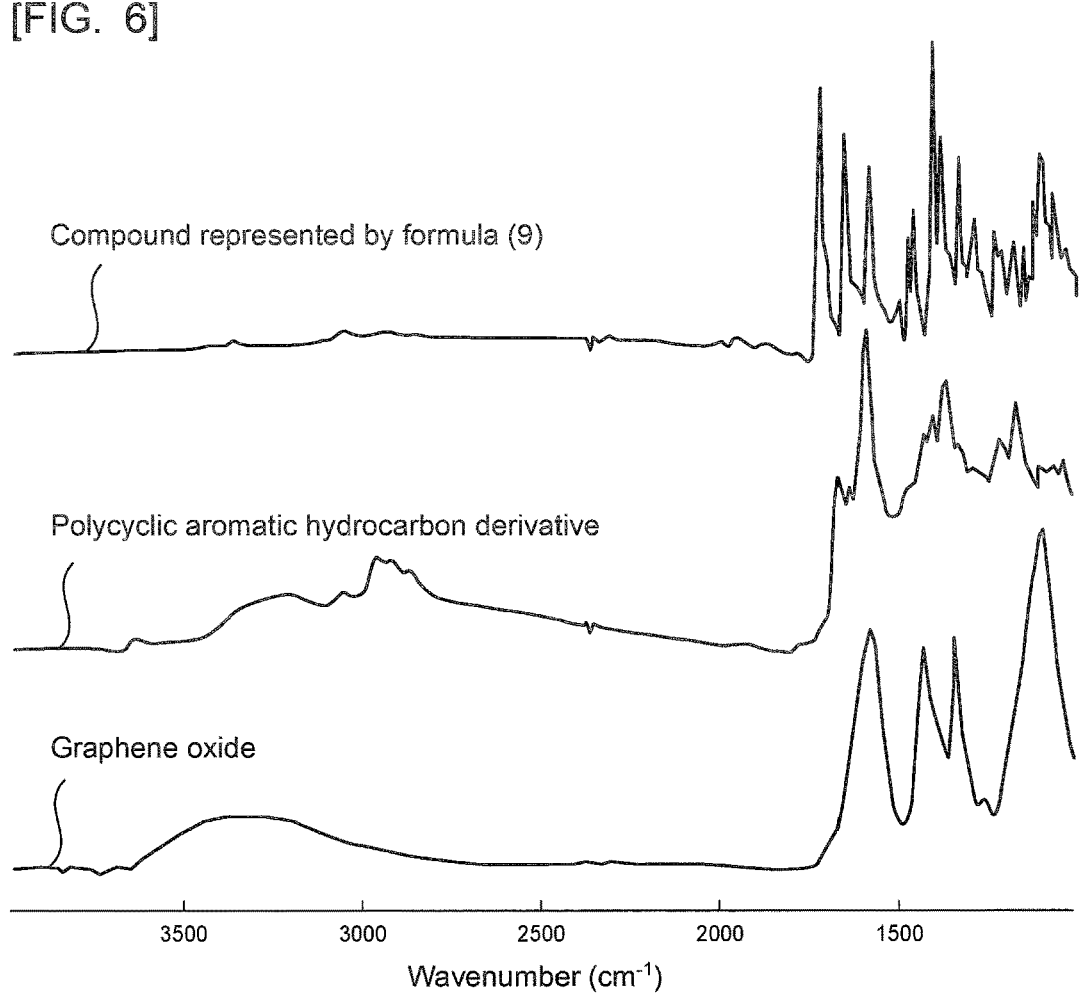

[FIG. 7]
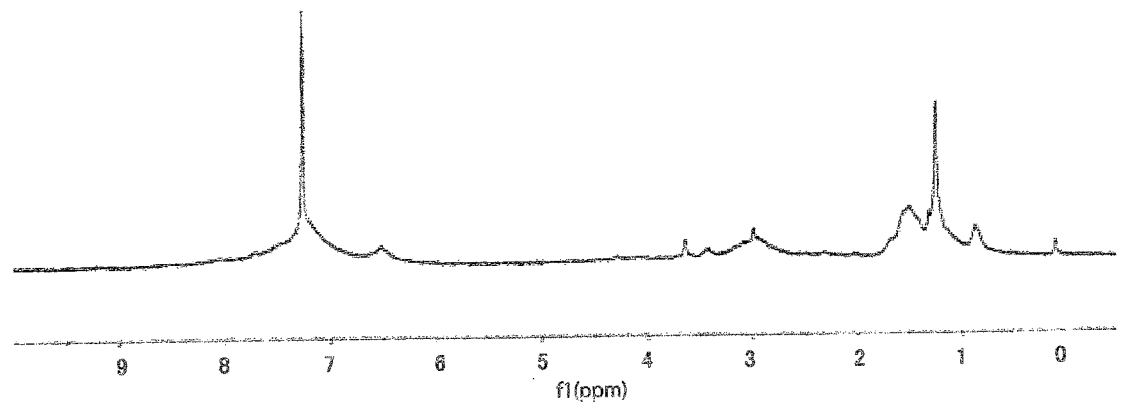
[FIG. 8]
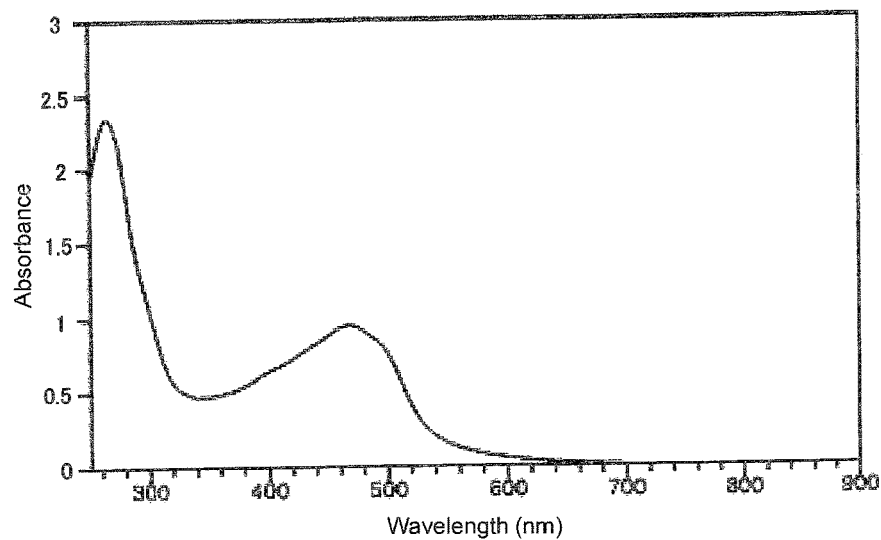
[FIG. 9]
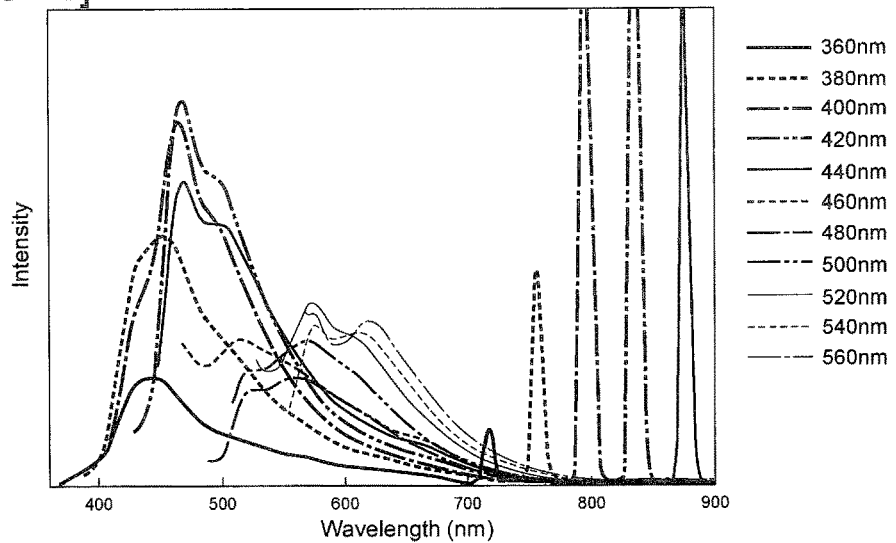

[FIG. 10]
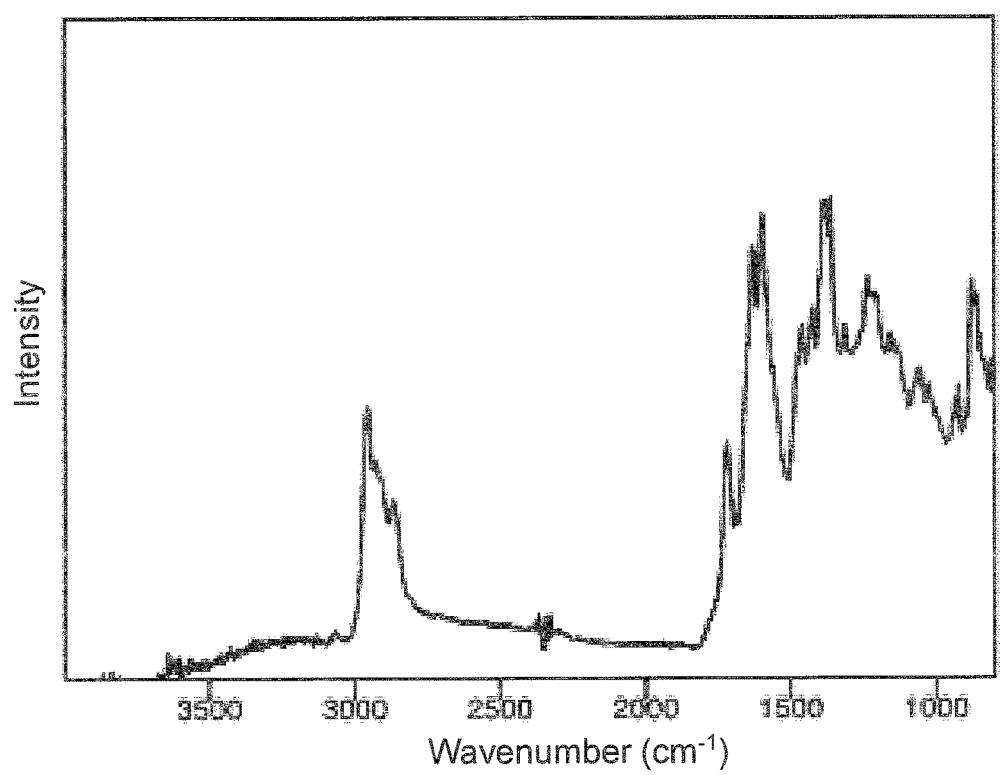
[FIG. 11]
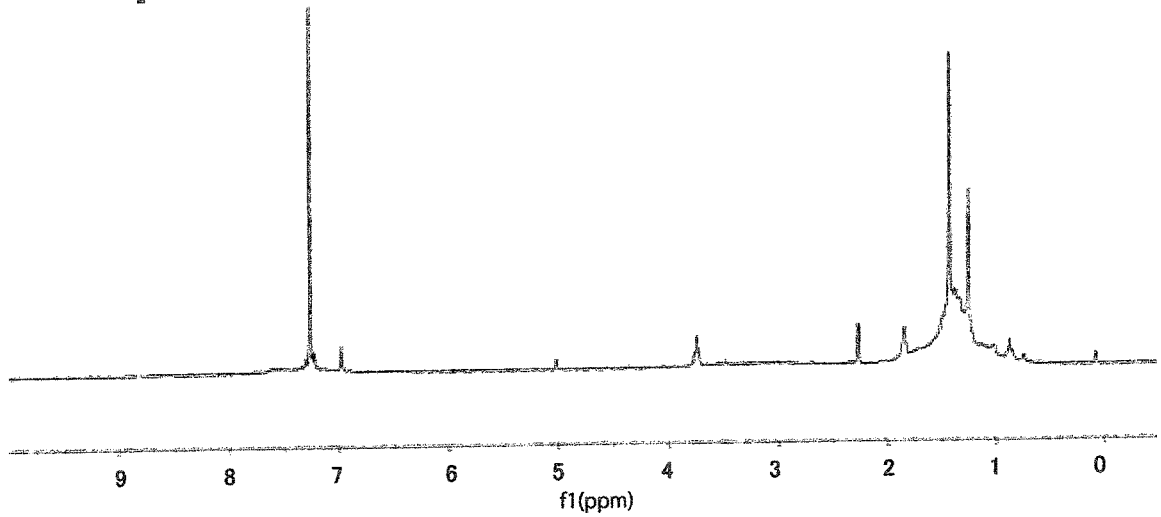

[FIG. 12]
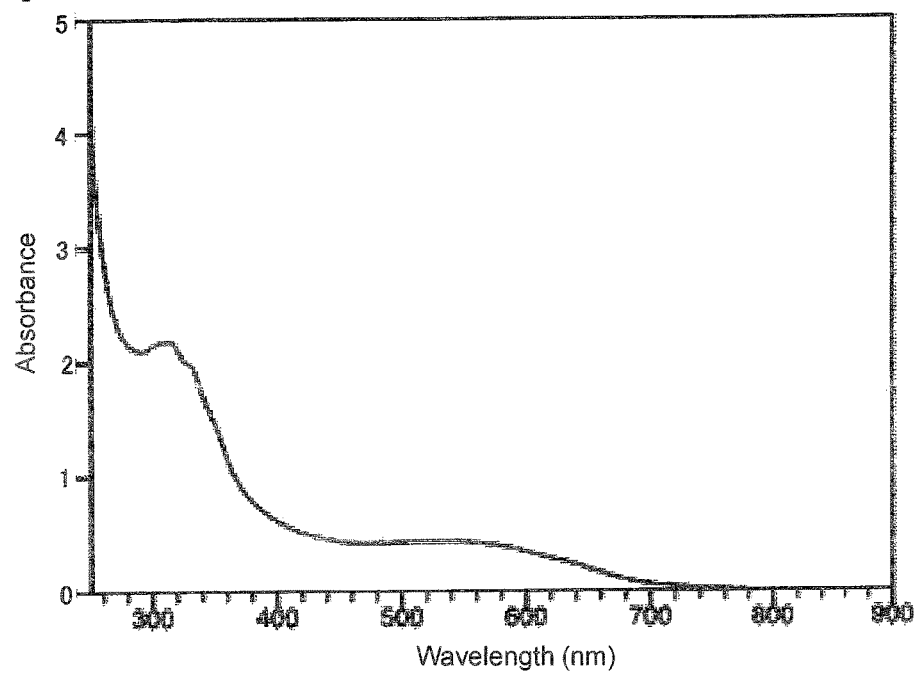
[FIG. 13]
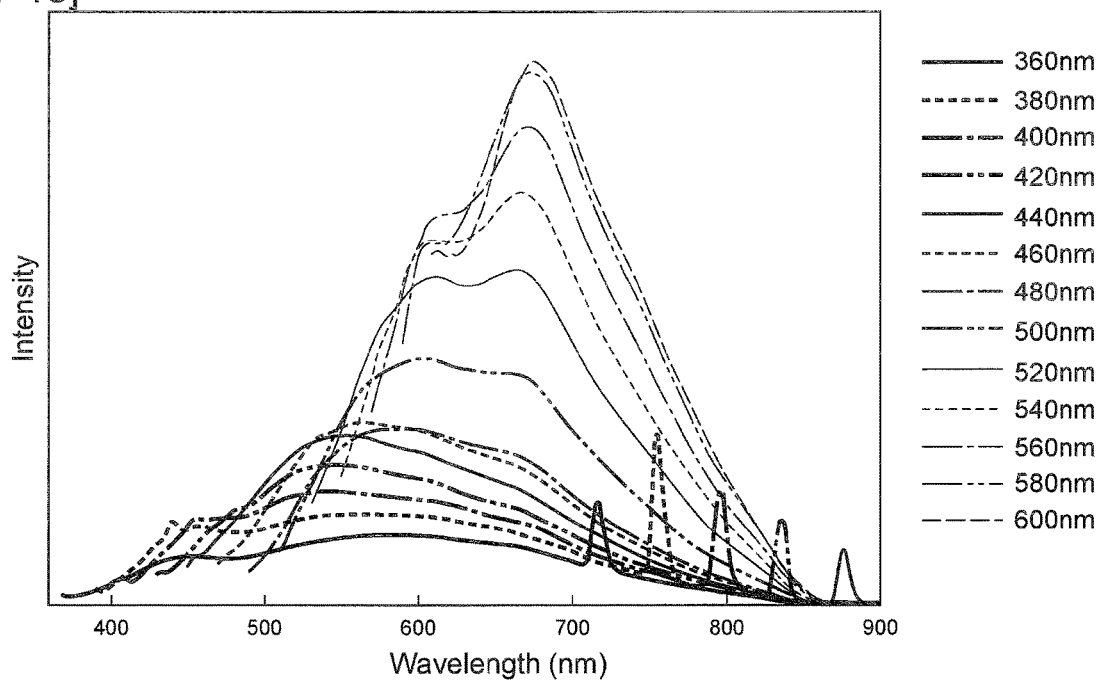

[FIG. 14]
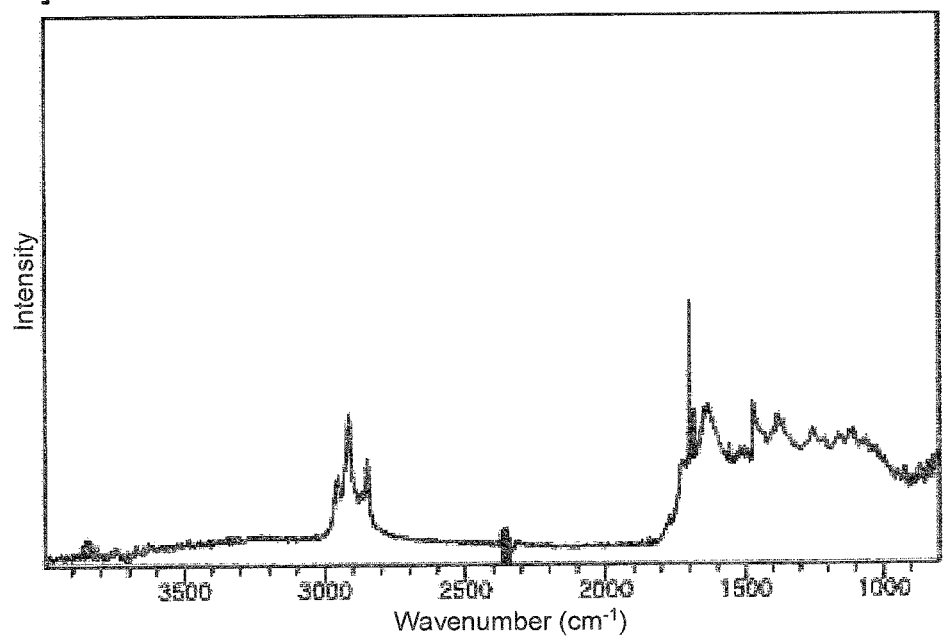
[FIG. 15]
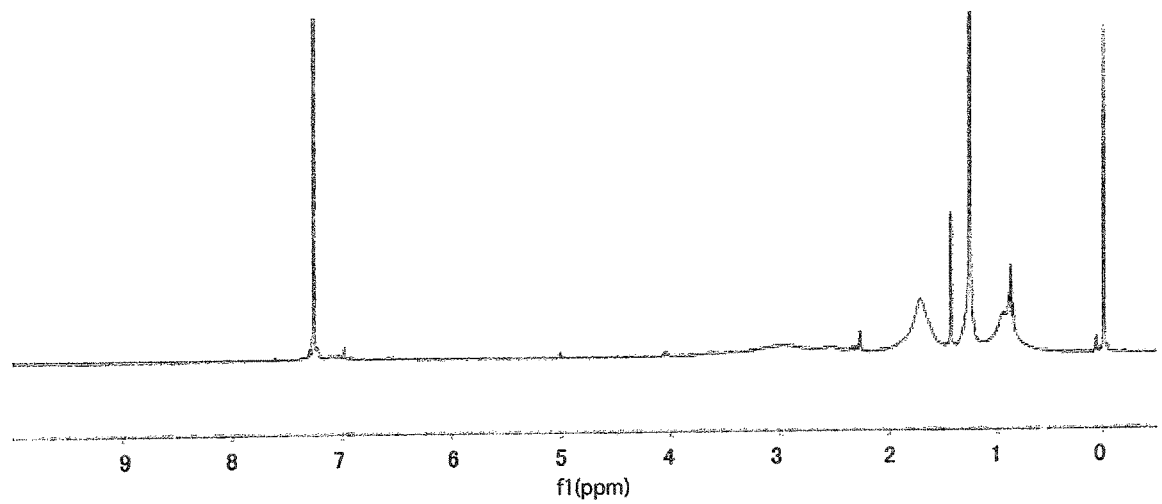

[FIG. 16]
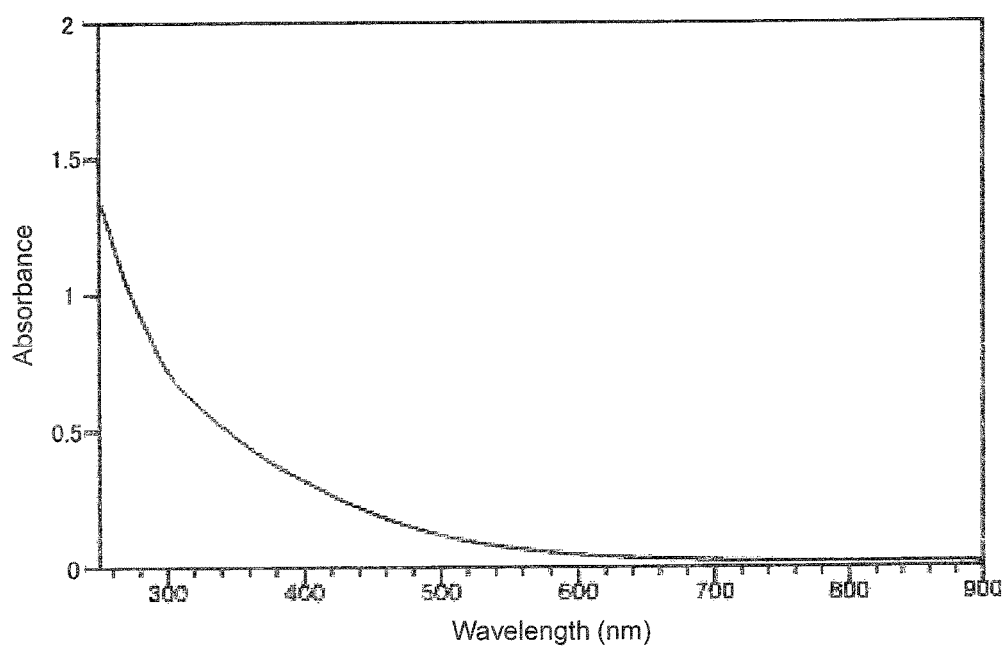
[FIG. 17]
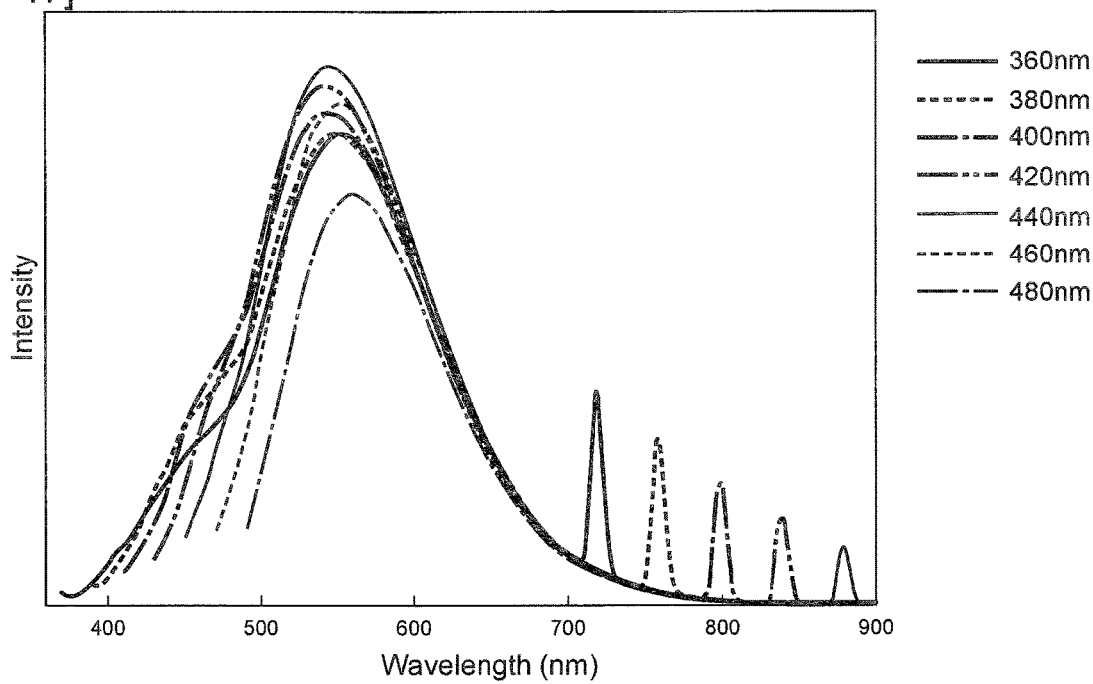

[FIG. 18]
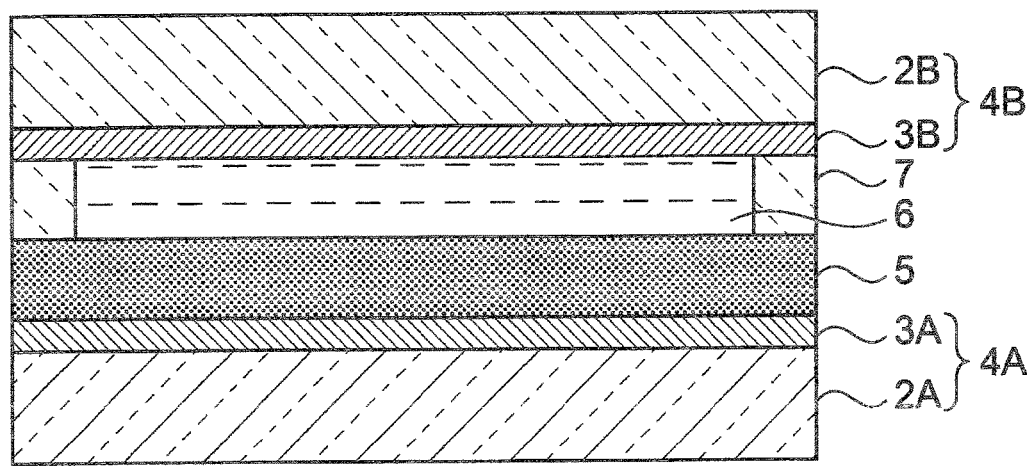

POLYCYCLIC AROMATIC HYDROCARBON DERIVATIVE, FLUORESCENT MATERIAL, PHOSPHORESCENT MATERIAL, AND LIGHT-MODULATING MATERIAL

TECHNICAL FIELD

The present invention relates to a polycyclic aromatic hydrocarbon derivative, and a fluorescent material, a phosphorescent material, and a light-modulating material that contain the polycyclic aromatic hydrocarbon derivative.

BACKGROUND ART

Conventionally, an organic electrochromic material has been used as a light-modulating material for blocking light having a specific wavelength to adjust the transmittance or the hue. The organic electrochromic material is being used in various fields including, for example, interior members such as a partition, a fusuma door, a shoji screen, a curtain, and a table, construction members such as window glass, members of a transport device and a vehicle device for a vehicle, an aircraft, and the like, and electronic parts such as electronic paper.

As such an organic electrochromic material, for example, Patent Document 1 below discloses a polyacetylene compound having a specific structure. The polyacetylene compound has a substituent containing a polycyclic aromatic hydrocarbon with less aromatic rings, such as a naphthalene group, a phenanthrene group, a pyrenyl group, or an anthracene group. Patent Document 1 describes that the polyacetylene compound that has one or more substituents containing a polycyclic aromatic hydrocarbon is capable of changing the light transmittance in a wide wavelength region, in response to a chemical stimulus or an electric stimulus, or a physical stimulus involving, for example, pressure or temperature.

RELATED ART DOCUMENT

Patent Document

Patent Document 1: WO 2007/061061

SUMMARY OF THE INVENTION

Problems to be Solved by the Invention

However, the polyacetylene compound in Patent Document 1 that has a substituent containing a polycyclic aromatic hydrocarbon has a problem that it has trouble being used in a hot season such as summer because it lets infrared light therethrough when blocking visible light. Many light-modulating materials other than the polyacetylene compound have also been studied. Any material, however, is insufficient in light modulation and still has a problem of, for example, being low in long-term stability.

The present invention has been made in view of the circumstances described above, and an object of the present invention is to provide a new polycyclic aromatic hydrocarbon derivative.

Another object of the present invention is to provide a fluorescent material, a phosphorescent material, and a light-modulating material that contain the polycyclic aromatic hydrocarbon derivative.

Means for Solving the Problems

A polycyclic aromatic hydrocarbon derivative according to the present invention is a derivative of a polycyclic aromatic hydrocarbon having 6 or more aromatic rings and has a substituent represented by the following formula (1).
[Chemical 1]

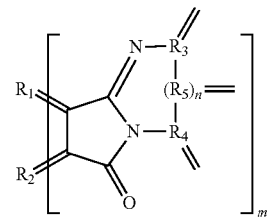

Formula (1)

(In the formula (1), $R_1$ and $R_2$ are carbon atoms of the aromatic rings in the polycyclic aromatic hydrocarbon, and $R_3$ to $R_5$ are carbon atoms of an aromatic ring or a heterocyclic ring in a group having the aromatic ring or the heterocyclic ring. n is 0 or 1, and m is the number of substituents.)

In a specific aspect of the polycyclic aromatic hydrocarbon derivative according to the present invention, the substituent is a substituent represented by the following formula (2).
[Chemical 2]

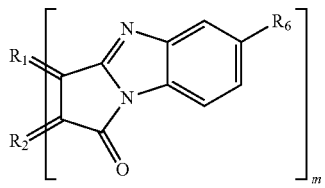

Formula (2)

(In the formula (2), $R_1$ and $R_2$ are carbon atoms of the aromatic rings in the polycyclic aromatic hydrocarbon. $R_6$ is a hydrogen atom, an alkyl group having 1 to 20 carbon atoms, an alkoxy group (with an alkyl group having 1 to 20 carbon atoms), a cyano group, a nitro group, an amino group, an acylamino group, an alkylcarbonyl group, an arylcarbonyl group, or an acetoxy group. m is the number of substituents.)

In another specific aspect of the polycyclic aromatic hydrocarbon derivative according to the present invention, the substituent is a substituent represented by the following formula (3).
[Chemical 3]

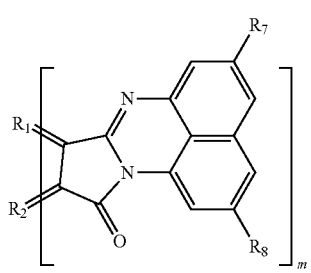

Formula (3)

(In the formula (3), $R_1$ and $R_2$ are carbon atoms of the aromatic rings in the polycyclic aromatic hydrocarbon. $R_7$ and $R_8$ are each a hydrogen atom, an alkyl group having 1 to 20 carbon atoms, an alkoxy group (with an alkyl group having 1 to 20 carbon atoms), a cyano group, a nitro group, an amino group, an acylamino group, an alkylcarbonyl group, an arylcarbonyl group, or an acetoxy group. m is the number of substituents.)

In another specific aspect of the polycyclic aromatic hydrocarbon derivative according to the present invention, the substituent is a substituent represented by the following formula (10).

[Chemical 4]

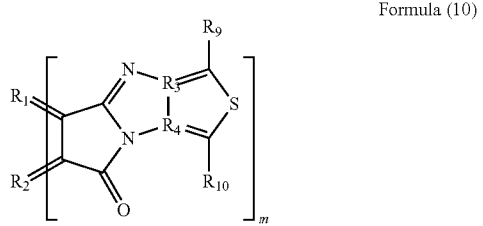

Formula (10)

(In the formula (10), $R_1$ and $R_2$ are carbon atoms of the aromatic rings in the polycyclic aromatic hydrocarbon. $R_3$ and $R_4$ are carbon atoms of an aromatic ring or a heterocyclic ring in a group having the aromatic ring or the heterocyclic ring. $R_9$ and $R_{10}$ are each a hydrogen atom, an alkyl group having 1 to 20 carbon atoms, an alkoxy group (with an alkyl group having 1 to 20 carbon atoms), a cyano group, a nitro group, an amino group, an acylamino group, an alkylcarbonyl group, an arylcarbonyl group, or an acetoxy group. m is the number of substituents.)

In another specific aspect of the polycyclic aromatic hydrocarbon derivative according to the present invention, the polycyclic aromatic hydrocarbon derivative has a plane-direction dimension of 100 nm or less.

A fluorescent material according to the present invention contains the polycyclic aromatic hydrocarbon derivative formed according to the present invention.

A phosphorescent material according to the present invention contains the polycyclic aromatic hydrocarbon derivative formed according to the present invention.

A light-modulating material according to the present invention contains the polycyclic aromatic hydrocarbon derivative formed according to the present invention.

Effect of the Invention

According to the present invention, it is possible to provide a new polycyclic aromatic hydrocarbon derivative, and a fluorescent material, a phosphorescent material, and a light-modulating material that contain the polycyclic aromatic hydrocarbon derivative.

BRIEF DESCRIPTION OF DRAWINGS

FIG. 1 is a reaction scheme for describing one exemplary method of producing a polycyclic aromatic hydrocarbon derivative according to the present invention.

FIG. 2 is a diagram showing a FT-IR spectrum of a polycyclic aromatic hydrocarbon derivative obtained in Example 1.

FIG. 3 is a diagram showing a $^1$H-NMR spectrum of the polycyclic aromatic hydrocarbon derivative obtained in Example 1.

FIG. 4 is a diagram showing an absorption spectrum of the polycyclic aromatic hydrocarbon derivative obtained in Example 1.

FIG. 5 is a diagram showing fluorescence spectra of the polycyclic aromatic hydrocarbon derivative obtained in Example 1.

FIG. 6 is a diagram showing a FT-IR spectrum of a polycyclic aromatic hydrocarbon derivative obtained in Example 2.

FIG. 7 is a diagram showing a $^1$H-NMR spectrum of the polycyclic aromatic hydrocarbon derivative obtained in Example 2.

FIG. 8 is a diagram showing an absorption spectrum of the polycyclic aromatic hydrocarbon derivative obtained in Example 2.

FIG. 9 is a diagram showing fluorescence spectra of the polycyclic aromatic hydrocarbon derivative obtained in Example 2.

FIG. 10 is a diagram showing a FT-IR spectrum of a polycyclic aromatic hydrocarbon derivative obtained in Example 3.

FIG. 11 is a diagram showing a $^1$H-NMR spectrum of the polycyclic aromatic hydrocarbon derivative obtained in Example 3.

FIG. 12 is a diagram showing an absorption spectrum of the polycyclic aromatic hydrocarbon derivative obtained in Example 3.

FIG. 13 is a diagram showing fluorescence spectra of the polycyclic aromatic hydrocarbon derivative obtained in Example 3.

FIG. 14 is a diagram showing a FT-IR spectrum of a polycyclic aromatic hydrocarbon derivative obtained in Example 4.

FIG. 15 is a diagram showing a $^1$H-NMR spectrum of the polycyclic aromatic hydrocarbon derivative obtained in Example 4.

FIG. 16 is a diagram showing an absorption spectrum of the polycyclic aromatic hydrocarbon derivative obtained in Example 4.

FIG. 17 is a diagram showing fluorescence spectra of the polycyclic aromatic hydrocarbon derivative obtained in Example 4.

FIG. 18 is a schematic front sectional view showing a light-modulating laminate as one exemplary case of using the polycyclic aromatic hydrocarbon derivative according to the present invention.

MODES FOR CARRYING OUT THE INVENTION

Hereinafter, the present invention is described in detail.

A polycyclic aromatic hydrocarbon derivative according to the present invention is a derivative of a polycyclic aromatic hydrocarbon having 6 or more aromatic rings. The polycyclic aromatic hydrocarbon derivative has a substituent represented by the following formula (1).

[Chemical 5]

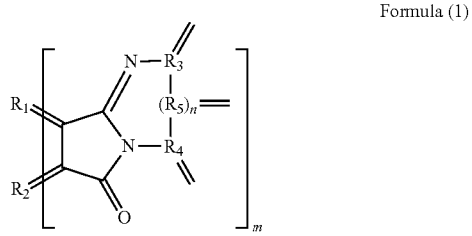

Formula (1)

In the formula (1), $R_1$ and $R_2$ are carbon atoms derived from the aromatic rings in the polycyclic aromatic hydrocarbon. Accordingly, $R_1$ and $R_2$ are not contained in the substituent, meaning that the polycyclic aromatic hydrocarbon containing $R_1$ and $R_2$ is provided. $R_3$ to $R_5$ are carbon atoms derived from an aromatic ring or a heterocyclic ring in a group having the aromatic ring or the heterocyclic ring. This means that the group is provided that has an aromatic ring or a heterocyclic ring containing $R_3$ to $R_5$. n is 0 or 1. Accordingly, $R_5$ need not be provided. m means the number of substituents of the polycyclic aromatic hydrocarbon derivative. The number of substituents m is preferably 3 or more, more preferably 5 or more and preferably 30 or less, more preferably 20 or less. When the number of substituents m is the above lower limit or more, the polycyclic aromatic hydrocarbon derivative enables a further large variation in electron density by electron transfer between the substituent and the polycyclic aromatic hydrocarbon. When the number of substituents m is the above upper limit or less, the polycyclic aromatic hydrocarbon derivative allows near-infrared absorption and infrared absorption derived from the polycyclic aromatic hydrocarbon portion to effectively and further easily to work for practical use. Such a polycyclic aromatic hydrocarbon derivative further certainly emits light in a near-infrared region.

When n equals 0, examples of the substituent represented by the formula (1) include a substituent represented by the following formula (2).

[Chemical 6]

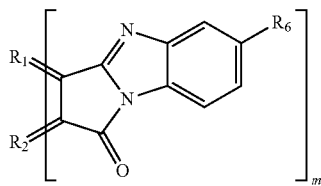

Formula (2)

In the formula (2), $R_1$ and $R_2$ are, in the same manner as above, carbon atoms derived from the aromatic rings in the polycyclic aromatic hydrocarbon. $R_6$ is a hydrogen atom, an alkyl group having 1 to 20 carbon atoms, an alkoxy group (with an alkyl group having 1 to 20 carbon atoms), a cyano group, a nitro group, an amino group, an acylamino group, an alkylcarbonyl group, an arylcarbonyl group, or an acetoxy group. m is, in the same manner as above, the number of substituents.

Specifically, when $R_6$ is a hydrogen atom, the substituent is a [d]9H-9-Oxo-benzo[4,5]imidazo[2,1-a]pyrro group. When $R_6$ is a methoxy group, the polycyclic aromatic hydrocarbon derivative is a compound represented by the following formula (4). It is to be noted that the formula (4), the following chemical formulae, and the drawings do not sometimes show a double bond in an aromatic ring forming graphene or the polycyclic aromatic hydrocarbon.

[Chemical 7]

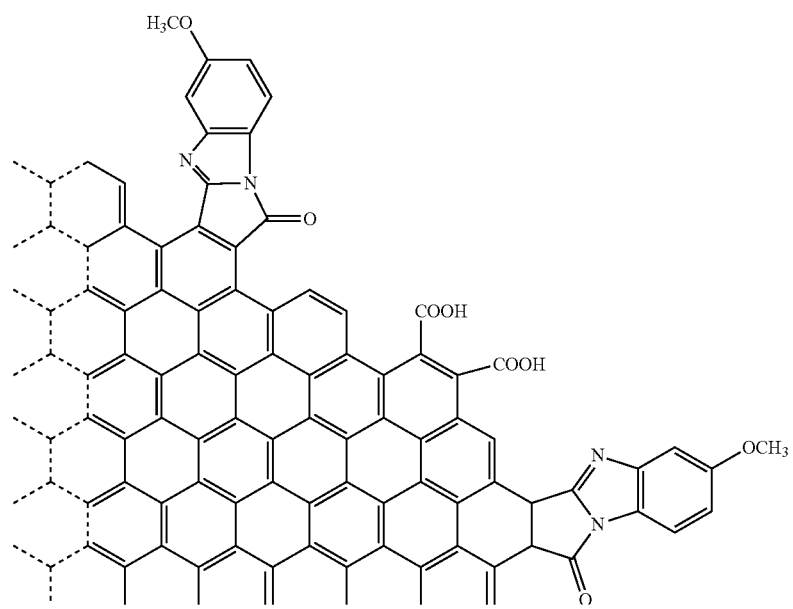

Formula (4)

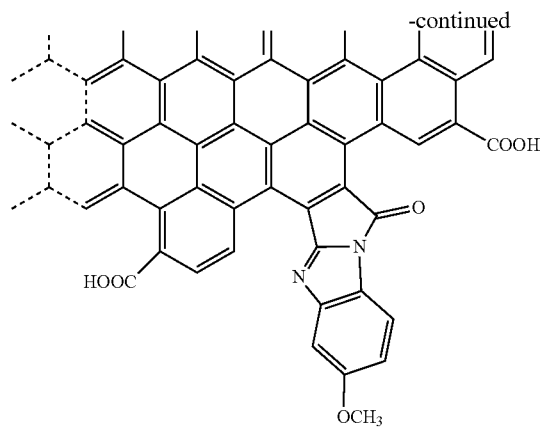

When n equals 0, the substituent may be a substituent represented by the following formula (10). That is, the group containing $R_3$ to $R_5$ in the formula (1) may be a group having a heterocyclic ring containing a sulfur atom. Examples of a compound having the substituent represented by the following formula (10) include a compound represented by the following formula (5). Naturally, the group containing $R_3$ to $R_5$ in the formula (1) may be a group having a heterocyclic ring containing a nitrogen atom.

[Chemical 8]

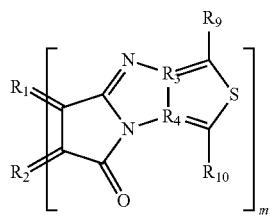

Formula (10)

In the formula (10), $R_1$ and $R_2$ are carbon atoms of the aromatic rings in the polycyclic aromatic hydrocarbon, and $R_3$ and $R_4$ are carbon atoms of an aromatic ring or a heterocyclic ring in a group having the aromatic ring or the heterocyclic ring. $R_9$ and $R_{10}$ are each a hydrogen atom, an alkyl group having 1 to 20 carbon atoms, an alkoxy group (with an alkyl group having 1 to 20 carbon atoms), a cyano group, a nitro group, an amino group, an acylamino group, an alkylcarbonyl group, an arylcarbonyl group, or an acetoxy group. m is the number of substituents.

[Chemical 9]

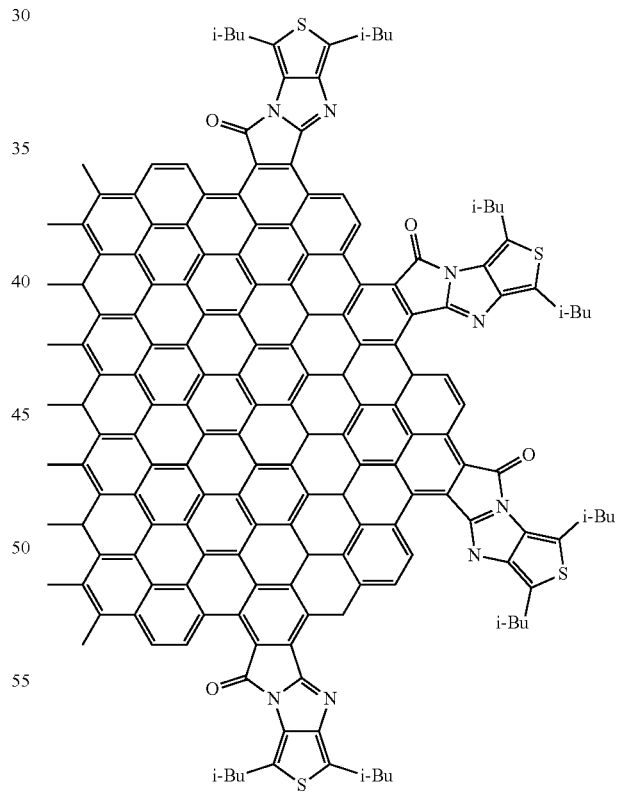

Formula (5)

In the formula (5), i-Bu is an isobutyl group.

When n equals 1, examples of the substituent represented by the formula (1) include a substituent represented by the following formula (3).

[Chemical 10]

Formula (3)

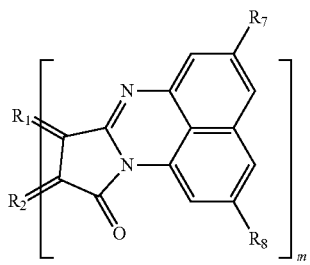

In the formula (3), $R_1$ and $R_2$ are, in the same manner as above, carbon atoms derived from the aromatic rings in the polycyclic aromatic hydrocarbon. $R_7$ and $R_8$ are each a hydrogen atom, an alkyl group having 1 to 20 carbon atoms, an alkoxy group (with an alkyl group having 1 to 20 carbon atoms), a cyano group, a nitro group, an amino group, an acylamino group, an alkylcarbonyl group, an arylcarbonyl group, or an acetoxy group. m is, in the same manner as above, the number of substituents.

Specifically, when $R_7$ and $R_8$ are hydrogen atoms, the substituent is a [d]11H-11-Oxo-Perimidino[2,1-a]pyrro group. That is, the polycyclic aromatic hydrocarbon derivative is a compound represented by the following formula (6).

[Chemical 11]

Formula (6)

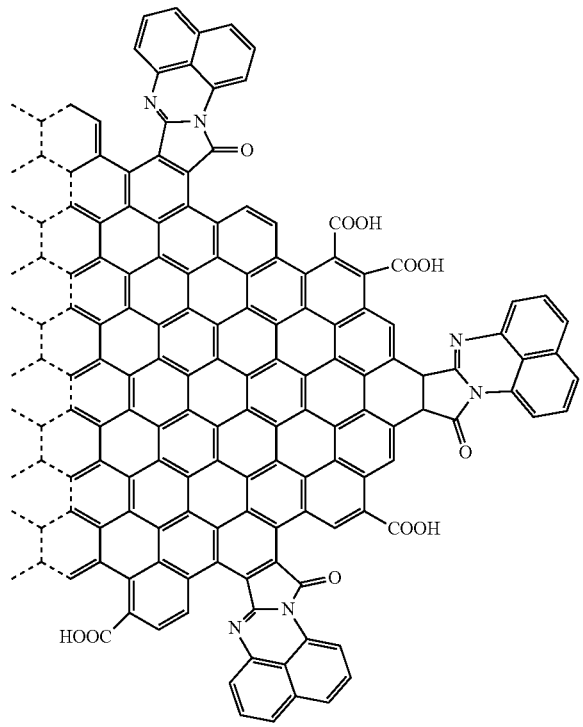

When $R_7$ and $R_8$ are tertiary butyl (t-Bu) groups, the polycyclic aromatic hydrocarbon derivative is a compound represented by the following formula (7).

[Chemical 12]

Formula (7)

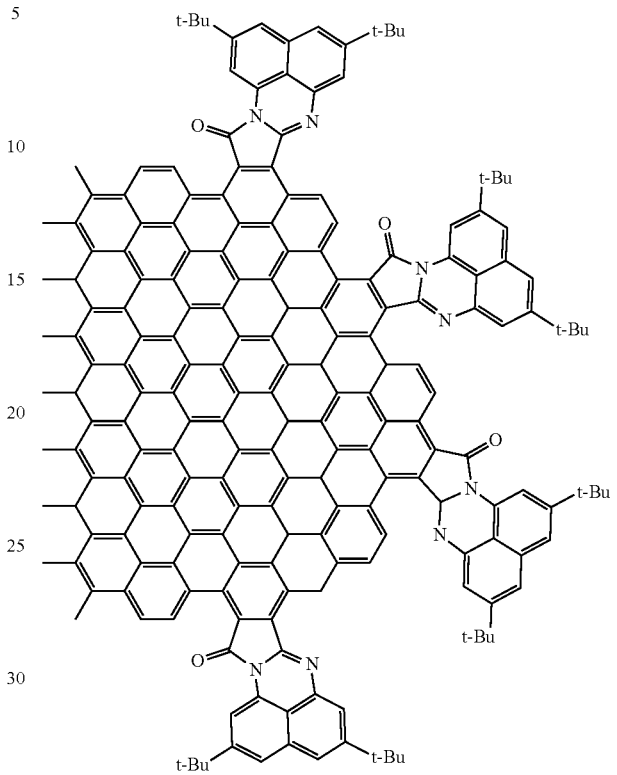

In the present invention, the number of aromatic rings in the polycyclic aromatic hydrocarbon forming the polycyclic aromatic hydrocarbon derivative is preferably 6 or more, more preferably 10 or more and preferably 10000 or less, more preferably 500 or less. When the number of aromatic rings is the above lower limit or more, the polycyclic aromatic hydrocarbon derivative shows aromatic ring-based absorption of light in an infrared region and shows no sublimation to facilitate formation of a stable coating film. In addition, such a polycyclic aromatic hydrocarbon derivative also facilitates controlling association between polycyclic aromatic hydrocarbons performed for function control. In addition, such a polycyclic aromatic hydrocarbon derivative further improves its solubility.

When the number of aromatic rings is the above upper limit or less, the aromatic ring derivative has good balance between the number of substituents and the number of aromatic rings to facilitate acquisition of a functional effect derived from the number of substituents and facilitate controlling the degree of association between polycyclic aromatic hydrocarbons.

Examples of the polycyclic aromatic hydrocarbon include coronene, ovalene, anthanthrene, a circulene, dicoronylene, a helicene, kekulene, zethrene, trinaphthylene, heptaphene, and heptacene. These polycyclic aromatic hydrocarbons may be used alone or in combination of a plurality thereof.

The polycyclic aromatic hydrocarbon may be graphene or graphene oxide. The polycyclic aromatic hydrocarbon may be a laminate of graphene sheets, i.e., flaked graphite or flaked graphite oxide. In this case, it is possible to set the number of laminated graphene sheets at, for example, 2 layers to 100 layers.

In the present invention, the shape of the polycyclic aromatic hydrocarbon derivative is not particularly limited, and examples thereof include a sheet shape and a plane-direction elongated ribbon shape. The plane-direction is a direction along a main surface of the polycyclic aromatic hydrocarbon derivative.

In the present invention, the polycyclic aromatic hydrocarbon derivative has a plane-direction dimension of preferably 1 nm or more, more preferably 5 nm or more and preferably 500 nm or less, more preferably 100 nm or less. The plane-direction dimension refers to a maximum dimension in the plane direction.

When the plane-direction dimension is the above lower limit or more, the polycyclic aromatic hydrocarbon derivative enables a further large variation in electron density by electron transfer between the substituent and the polycyclic aromatic hydrocarbon. This results in further facilitating control of the absorption wavelength and the light emission wavelength. When the plane-direction dimension is the above upper limit or less, the polycyclic aromatic hydrocarbon derivative allows an optical function derived from the substituent to effectively and further easily to work for practical use.

In the present invention, the polycyclic aromatic hydrocarbon derivative has an aspect ratio of preferably 3 or more and preferably 330 or less. The aspect ratio is obtained by dividing the plane-direction maximum dimension of the polycyclic aromatic hydrocarbon derivative by the thickness of the polycyclic aromatic hydrocarbon derivative (plane-direction maximum dimension/thickness).

It is possible to obtain the plane-direction dimension and the aspect ratio of the polycyclic aromatic hydrocarbon derivative by using, for example, an electron microscope or a scanning probe microscope (SPM).

In the present invention, the polycyclic aromatic hydrocarbon derivative may have another substituent. The polycyclic aromatic hydrocarbon derivative may have a substituent such as a hydroxyl group, a phenoxy group, a carboxyl group, a carbonyl group, a glycidyl group, an oxetanyl group, an ether group, an ester group, an acryloyl group, a methacryloyl group, a styryl group, or a vinyl group. Alternatively, the polycyclic aromatic hydrocarbon derivative may have a substituent such as an allyl group, an amino group, a nitro group, a cyano group, an acylamino group, an isocyanate group, a mercapto group, a sulfonate group, a silyl group, or an alkoxysilyl group.

The polycyclic aromatic hydrocarbon derivative according to the present invention enables a large variation in electron density by electron transfer between the polycyclic aromatic hydrocarbon and the substituent represented by the formula (1). Such a polycyclic aromatic hydrocarbon derivative according to the present invention is capable of controlling the light transmittance in a wide region from visible light to infrared light, in response to a chemical stimulus or an electric stimulus, or a physical stimulus involving, for example, pressure or temperature. Such a polycyclic aromatic hydrocarbon derivative also has excellent long-term stability. Thus, it is possible to suitably use the polycyclic aromatic hydrocarbon derivative according to the present invention as a light-modulating material. In addition, the polycyclic aromatic hydrocarbon derivative according to the present invention has fluorescent characteristics and phosphorescent characteristics. Thus, it is possible to suitably use the polycyclic aromatic hydrocarbon derivative also as a fluorescent material and a phosphorescent material.

It is possible to obtain the polycyclic aromatic hydrocarbon derivative according to the present invention by, for example, a reaction scheme shown in FIG. 1. Here, the compound represented by the formula (4) is described as an example. As shown in FIG. 1, first prepared is a polycyclic aromatic hydrocarbon that contains an aromatic ring having two carboxyl groups. The aromatic ring desirably has the two carboxyl groups at ortho position. It is possible to obtain this polycyclic aromatic hydrocarbon that contains an aromatic ring having two carboxyl groups by, for example, hydrolyzing an acid anhydride of a polycyclic aromatic hydrocarbon. It is also possible to use graphene oxide or flaked graphite oxide. Graphene oxide or flaked graphite oxide may be used after subjected to oxidative scission. It is possible to produce graphene oxide or flaked graphite oxide by a conventionally known production method such as the Hummers method. This polycyclic aromatic hydrocarbon that contains an aromatic ring having two carboxyl groups may be one obtained by hydrolyzing an acid anhydride of a condensed polycyclic aromatic hydrocarbon in which a plurality of aromatic rings are condensed. Alternatively, this polycyclic aromatic hydrocarbon that contains an aromatic ring having two carboxyl groups may be graphene oxide or flaked graphite oxide, or one obtained by subjecting graphene oxide or flaked graphite oxide to oxidative scission.

On the other hand, a compound is prepared that has an aromatic ring or a heterocyclic ring substituted by at least two amino groups. When the compound has a plurality of aromatic rings or heterocyclic rings, one aromatic ring or heterocyclic ring may be substituted by at least two amino groups, or two or more aromatic rings or heterocyclic rings may be substituted by at least two amino groups.

Examples of such a compound include diamines such as 1,2-diaminobenzene, 4-methoxy-1,2-diaminobenzene, 4-cyano-1,2-diaminobenzene, 4-nitro-1,2-diaminobenzene, naphthalene-1,8-diamine, and phenanthrene-9,10-diamine. It is also possible to use, for example, a diamine such as pyrene-4,5-diamine or 3,6-ditertiarybutyl-naphthalene-1,8-diamine, or 2,4-diaminopyridine, 3,4-diaminothiophene, or 3,4-diamino-2,5-ditertiarybutylthiophene.

Next, as shown in FIG. 1, the polycyclic aromatic hydrocarbon that contains an aromatic ring having two carboxyl groups is reacted with the compound having an aromatic ring or a heterocyclic ring substituted by at least two amino groups. This procedure is capable of giving the polycyclic aromatic hydrocarbon derivative according to the present invention.

As shown in the examples described later, it is possible to perform the reaction in the presence of, for example, oxalyl chloride, N,N-dimethylformamide, or triethylamine.

For example, the polycyclic aromatic hydrocarbon that contains an aromatic ring having two carboxyl groups and oxalyl chloride are heated in the presence of a catalyst quantity of N,N-dimethylformamide, at 60° C. for 4 days. After removal of oxalyl chloride, the polycyclic aromatic hydrocarbon that contains an aromatic ring having carboxyl groups and has been made into an acid chloride is added into N,N-dimethylformamide, to which triethylamine and a catalyst quantity of N,N-dimethyl-4-aminopyridine is added. Thereafter, the compound is added that has an aromatic ring or a heterocyclic ring substituted by two amino groups. This solution is stirred at 80° C. for 4 days. After removal of the solvent, purification through bio beads, with tetrahydrofuran used as a developing solvent, is performed to be capable of giving the aimed polycyclic aromatic hydrocarbon derivative. When the reaction is not completed, acetic acid is added, followed by heating, to give a group or a product.

It is possible to confirm the production of the polycyclic aromatic hydrocarbon derivative according to the present invention with, for example, a Fourier transform infrared spectrophotometer (FT-IR) or a nuclear magnetic resonator (NMR).

FIG. 18 is a schematic front sectional view showing a light-modulating laminate as one exemplary case of using the polycyclic aromatic hydrocarbon derivative according to the present invention.

As shown in FIG. 18, a light-modulating laminate 1 includes first and second supports 2A and 2B. The light-modulating laminate 1 has a configuration in which a light-modulating film 5 described later is sandwiched between the first and second supports 2A and 2B. In the present embodiment, the first and second supports 2A and 2B are glass substrates. The first and second supports 2A and 2B may be formed of an appropriate material having high transparency, other than glass.

A first conductive film 3A is disposed on the first support 2A. As the first conductive film 3A, it is possible to use, for example, a transparent electrode such as ITO. The first support 2A and the first conductive film 3A form a first conductive film-attached substrate 4A. In the same manner, a second conductive film 3B is disposed on the second support 2B. The second support 2B and the second conductive film 3B form a second conductive film-attached substrate 4B. The second conductive film 3B is formed of the same material as the first conductive film 3A.

The light-modulating film 5 is disposed on the first conductive film 3A. The light-modulating material for a light-modulating film 5 contains the polycyclic aromatic hydrocarbon derivative according to the present invention. An electrolyte layer 6 is disposed on the light-modulating film 5. More specifically, a support member 7 disposed to surround the electrolyte layer 6 is disposed on the light-modulating film 5. The second conductive film-attached substrate 4B is disposed on the support member 7 to encapsulate the electrolyte layer 6.

The second conductive film 3B of the second conductive film-attached substrate 4B is positioned on the side of the support member 7 and the electrolyte layer 6. The first and second conductive films 3A and 3B are counter electrodes of the light-modulating laminate 1.

An electrolyte solution is sealed in a space surrounded by the light-modulating film 5, the second conductive film 3B, and the support member 7. The electrolyte solution is not particularly limited, and it is possible to use, for example, an electrolyte solution containing ethylene carbonate (EC), dimethyl carbonate (DMC), or the like as a solvent, and $LiPF_6$ or the like. Thus, the electrolyte layer 6 is disposed.

A voltage is applied to the light-modulating laminate 1 configured as described above to change the light transmittance at each wavelength. The electrolyte layer 6 need not necessarily be disposed. Naturally, however, the disposition of the electrolyte layer 6 as in the present embodiment enables an effective change in light transmittance.

Hereinafter, the present invention is made clear with reference to specific examples of the present invention and comparative examples. The present invention, however, is not limited to the following examples.

Example 1

First, graphene oxide was prepared by a method described in Document "J. J. Zhu, P. M. Ajayan, et al., Nano Lett., 2012, 12, 844-849."

Specifically, 1600 mL of a mixed acid (concentrated sulfuric acid:concentrated nitric acid=3:1 (volume ratio)) was poured into a 5-L three-necked flask, and 6.3 g of powder (particle size <20 μm) graphite (manufactured by Sigma-Aldrich Co. LLC.) was further charged into the flask. Subsequently, a Dimroth condenser was provided in one opening of the three-necked flask, and the other openings were provided with closed three-way cocks. The contents was, in this state, heated to 120° C. in an oil bath under stirring with a magnetic stirrer in an air atmosphere while cooling water was flowed, to react the contents for 24 hours. The resultant reactant was diluted with 2 L of ion-exchanged water. Then, the diluted solution was neutralized with sodium carbonate to give a pH close to 8 and thus give a neutralized treatment solution. The neutralized treatment solution was poured into a dialysis bag and subjected to a dialysis treatment for 3 days, and a treatment solution having a neutralization salt and the like removed therefrom was dried to give 2.5 g of graphene oxide.

With use of the graphene oxide prepared as described above, a polycyclic aromatic hydrocarbon derivative represented by the following formula (4) was synthesized.
[Chemical 13]

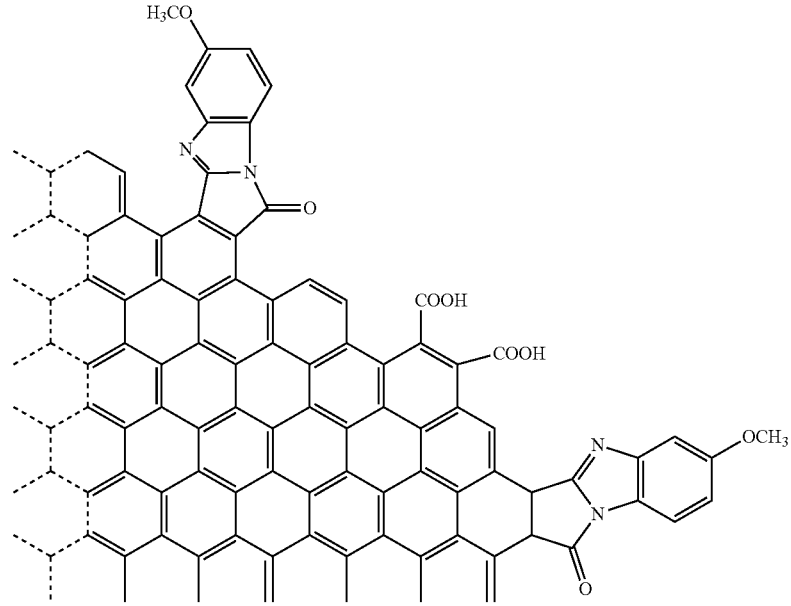

Formula (4)

-continued

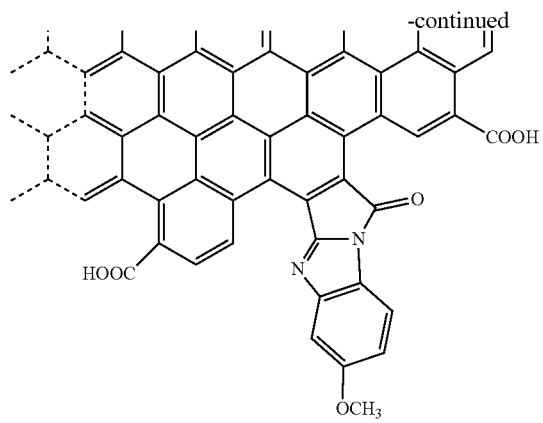

Specifically, a stir bar was placed in a 50-mL eggplant flask equipped with a three-way cock and they were baked with a heat gun under flowing argon gas. After cooling them, 111 mg of the graphene oxide prepared as described above were weighed into the eggplant flask in a dry box. After the weighing, the eggplant flask was taken out from the dry box, 6 mL of oxalyl chloride (manufactured by Sigma-Aldrich Co. LLC.) were added by syringe operation under a flow of argon, and 0.04 mL of dry N,N-dimethylformamide (DMF, manufactured by Sigma-Aldrich Co. LLC.) were further added. Next, the mixed liquid containing graphene oxide, oxalyl chloride, and DMF in the eggplant flask was subjected to an ultrasonic process for 2 hours with an ultrasonic processor (item No. "US-103," manufactured by SND Co., Ltd.). Then, the mixed liquid was subjected to operation of heating with hot water at 60° C. under stirring with a stirrer for 6 days. After the mixed liquid was thus reacted, 10 mL of dry DMF, 5 mL of triethylamine, and 450 mg of 4-methoxy-1,2-diaminobenzene were further added to the eggplant flask, and the mixed liquid was further reacted continuously with hot water at 80° C. in an argon atmosphere for 4 days. The resultant reactant was subjected to separation through a separating funnel with chloroform/an aqueous saturated NaCl solution to recover a chloroform recovery liquid. The chloroform recovery liquid was dried with mirabilite for 12 hours, and then chloroform was removed with an evaporator to give 200 mg of a polycyclic aromatic hydrocarbon derivative.

FIG. 2 is a diagram showing a FT-IR spectrum of the polycyclic aromatic hydrocarbon derivative obtained in Example 1. FIG. 2 also shows, for comparison, FT-IR spectra of a compound represented by the following formula (8) and unmodified graphene oxide. The FT-IR spectra were measured with a Fourier transform infrared spectrophotometer (item No. "FT/IR-4600," manufactured by JASCO Corporation) (the same measurement was performed also in the following examples).
[Chemical 14]

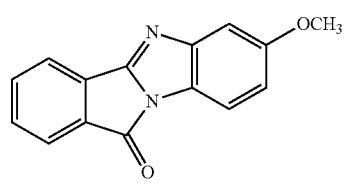

Formula (8)

As shown in FIG. 2, the resultant polycyclic aromatic hydrocarbon derivative was observed to have a shoulder peak at around 1600 cm$^{-1}$ in addition to a peak derived from graphene oxide. The shoulder peak exists at almost the same position as a peak of the compound represented by the formula (8), and the unmodified graphene oxide was not observed to have such a peak. Thus, it was clarified that the resultant polycyclic aromatic hydrocarbon derivative introduced the same substituent as the compound represented by the formula (8).

FIG. 3 is a diagram showing a $^1$H-NMR spectrum of the polycyclic aromatic hydrocarbon derivative obtained in Example 1. The $^1$H-NMR spectrum was measured with a nuclear magnetic resonator (item No. "Mercury-300," manufactured by Varian, Inc.) (the same measurement was performed also in the following examples). As shown in FIG. 3, the resultant $^1$H-NMR spectrum was observed to show a signal derived from a methoxy group at around 3.5 ppm to 4.0 ppm and a signal derived from an aromatic ring (partially overlapped with a signal of chloroform) at around 6.5 ppm to 7.5 ppm.

Accordingly, FIGS. 2 and 3 clarified the production of the polycyclic aromatic hydrocarbon derivative represented by the formula (4).

FIG. 4 is a diagram showing an absorption spectrum of the polycyclic aromatic hydrocarbon derivative obtained in Example 1. As shown in FIG. 4, the resultant polycyclic aromatic hydrocarbon derivative had an absorption band as far as around 700 nm.

FIG. 5 is a diagram showing fluorescence spectra of the polycyclic aromatic hydrocarbon derivative obtained in Example 1. FIG. 5 shows fluorescence spectra with exciting light having wavelengths of 360 nm to 560 nm. FIG. 5 understandably shows that the resultant polycyclic aromatic hydrocarbon derivative has maximum fluorescence intensity at around a wavelength of 550 nm.

The resultant polycyclic aromatic hydrocarbon derivative was measured for its plane-direction dimension and thickness with an atomic force microscope (AFM, manufactured by Agilent Technologies, Inc., trade name "PicoPlus5100"). As a result of the measurement performed 3 times, the average values of the plane-direction dimension and the aspect ratio were 51 nm and 23, respectively.

Example 2

Also in Example 2, graphene oxide was prepared in the same manner as in Example 1.

With use of the graphene oxide prepared as described above, a polycyclic aromatic hydrocarbon derivative represented by the following formula (6) was synthesized.
[Chemical 15]

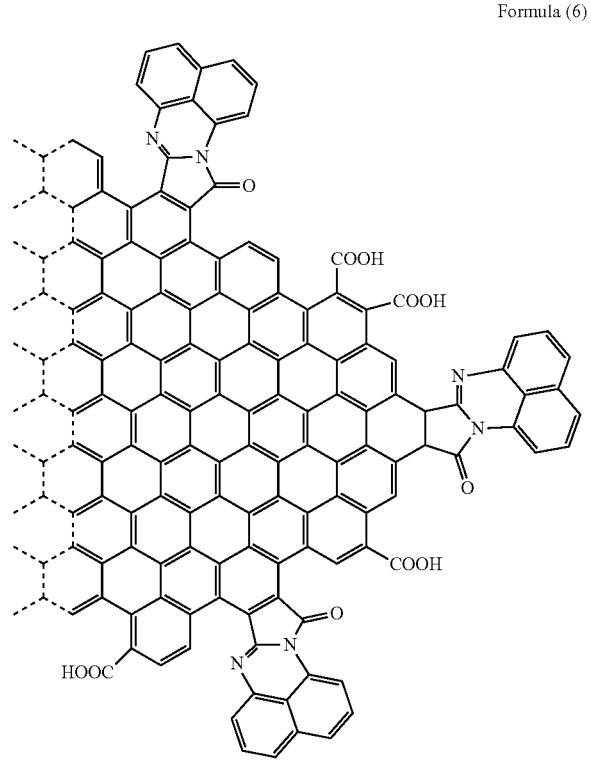

Formula (6)

Specifically, a stir bar was placed in a 50-mL eggplant flask equipped with a three-way cock and they were baked with a heat gun under flowing argon gas. After cooling them, 111 mg of the graphene oxide prepared in the same manner as in Example 1 were weighed into the eggplant flask in a dry box. After the weighing, the eggplant flask was taken out from the dry box, 6 mL of oxalyl chloride (manufactured by Sigma-Aldrich Co. LLC.) were added by syringe operation under a flow of argon, and 0.04 mL of dry N,N-dimethylformamide (DMF, manufactured by Sigma-Aldrich Co. LLC.) were further added. Next, the mixed liquid containing graphene oxide, oxalyl chloride, and DMF in the eggplant flask was subjected to an ultrasonic process for 2 hours with an ultrasonic processor (item No. "US-103," manufactured by SND Co., Ltd.). Then, the mixed liquid was subjected to operation of heating with hot water at 60° C. under stirring with a stirrer for 6 days. After the mixed liquid was thus reacted, 10 mL of dry DMF, 5 mL of triethylamine, and 450 mg of naphthalene-1,8-diamine were further added to the eggplant flask, and the mixed liquid was further reacted continuously with hot water at 80° C. in an argon atmosphere for 4 days. The resultant reactant was subjected to separation through a separating funnel with chloroform/an aqueous saturated NaCl solution to recover a chloroform recovery liquid. The chloroform recovery liquid was dried with mirabilite for 12 hours, and then chloroform was removed with an evaporator to give 161.5 mg of a polycyclic aromatic hydrocarbon derivative.

FIG. 6 is a diagram showing a FT-IR spectrum of the polycyclic aromatic hydrocarbon derivative obtained in Example 2. FIG. 6 also shows, for comparison, FT-IR spectra of a compound represented by the following formula (9) and unmodified graphene oxide.
[Chemical 16]

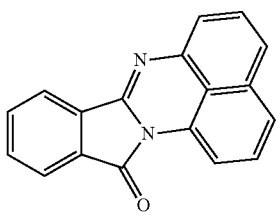

Formula (9)

As shown in FIG. 6, the resultant polycyclic aromatic hydrocarbon derivative was observed to have a shoulder peak at around 1600 cm$^{-1}$ to 1700 cm$^{-1}$ in addition to a peak derived from graphene oxide. The shoulder peak exists at almost the same position as a peak of the compound represented by the formula (9), and the unmodified graphene oxide was not observed to have such a peak. Thus, it was clarified that the resultant polycyclic aromatic hydrocarbon derivative introduced the same substituent as the compound represented by the formula (9).

FIG. 7 is a diagram showing a $^1$H-NMR spectrum of the polycyclic aromatic hydrocarbon derivative obtained in Example 2. As shown in FIG. 7, the resultant $^1$H-NMR spectrum was observed to show a signal derived from an aromatic ring at around 6.5 ppm to 8.0 ppm.

Accordingly, FIGS. 6 and 7 clarified the production of the polycyclic aromatic hydrocarbon derivative represented by the formula (6).

FIG. 8 is a diagram showing an absorption spectrum of the polycyclic aromatic hydrocarbon derivative obtained in Example 2. As shown in FIG. 8, the resultant polycyclic aromatic hydrocarbon derivative was observed to have another absorption band attributable to the aimed partial structure at around 470 nm, to clarify that the aimed structure was introduced into the graphene skeleton.

FIG. 9 is a diagram showing fluorescence spectra of the polycyclic aromatic hydrocarbon derivative obtained in Example 2. FIG. 9 shows fluorescence spectra with exciting light having wavelengths of 360 nm to 560 nm. FIG. 9 understandably shows that the resultant polycyclic aromatic hydrocarbon derivative has maximum fluorescence intensity at around a wavelength of 400 nm to 500 nm.

The resultant polycyclic aromatic hydrocarbon derivative was measured for its plane-direction dimension and thickness in the same manner as in Example 1, resulting in a plane-direction dimension of 60 nm and an aspect ratio of 200.

Example 3

Also in Example 3, graphene oxide was prepared in the same manner as in Example 1.

With use of the graphene oxide prepared as described above, a polycyclic aromatic hydrocarbon derivative represented by the following formula (7) was synthesized. In the formula (7), t-Bu represents a tertiary butyl group.

[Chemical 17]

Formula (7)

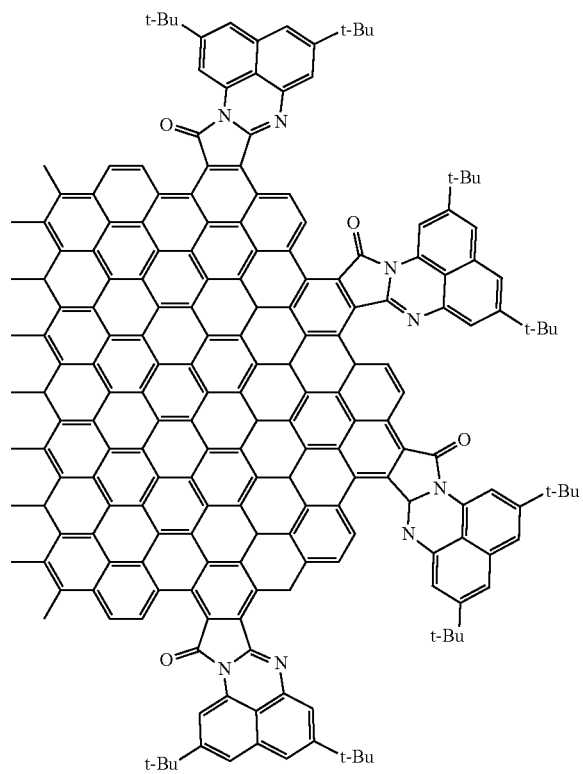

Specifically, a stir bar was placed in a 50-mL eggplant flask equipped with a three-way cock and they were baked with a heat gun under flowing argon gas. After cooling them, 106.5 mg of the graphene oxide prepared in the same manner as in Example 1 were weighed into the eggplant flask in a dry box. After the weighing, the eggplant flask was taken out from the dry box, 5 mL of oxalyl chloride (manufactured by Sigma-Aldrich Co. LLC.) were added by syringe operation under a flow of argon, and 0.10 mL of dry N,N-dimethylformamide (DMF, manufactured by Sigma-Aldrich Co. LLC.) were further added. Next, the mixed liquid containing graphene oxide, oxalyl chloride, and DMF in the eggplant flask was subjected to an ultrasonic process for 3 hours with an ultrasonic processor (item No. "US-103," manufactured by SND Co., Ltd.). Then, the mixed liquid was subjected to operation of heating with hot water at 60° C. under stirring with a stirrer for 4 days. After the mixed liquid was thus reacted, 5 mL of dry DMF, 5 mL of triethylamine, and 466 mg of 3,6-ditertiarybutyl-naphthalene-1,8-diamine were further added to the eggplant flask, and the mixed liquid was further reacted continuously with hot water at 80° C. in an argon atmosphere for 5 days. The resultant reactant was subjected to separation through a separating funnel with ethyl acetate/an aqueous saturated NaCl solution to recover an ethyl acetate recovery liquid. The ethyl acetate recovery liquid was dried with mirabilite for 12 hours, and then ethyl acetate was removed with an evaporator and purification was performed through a bio bead column (developing solvent: THF) to give 277.3 mg of a polycyclic aromatic hydrocarbon derivative.

FIG. 10 is a diagram showing a FT-IR spectrum of the polycyclic aromatic hydrocarbon derivative obtained in Example 3. As shown in FIG. 10, it was clarified that the resultant polycyclic aromatic hydrocarbon derivative has a peak derived from the substituent shown in the formula (7) in addition to a peak derived from graphene oxide.

FIG. 11 is a diagram showing a $^1$H-NMR spectrum of the polycyclic aromatic hydrocarbon derivative obtained in Example 3. As shown in FIG. 11, the resultant $^1$H-NMR spectrum was observed to show a signal derived from a t-Bu group at around 1 ppm to 1.5 ppm and a signal derived from an aromatic ring at around 6.5 ppm to 8.0 ppm.

Accordingly, FIGS. 10 and 11 clarified the production of the polycyclic aromatic hydrocarbon derivative represented by the formula (7).

FIG. 12 is a diagram showing an absorption spectrum of the polycyclic aromatic hydrocarbon derivative obtained in Example 3. As shown in FIG. 12, the resultant polycyclic aromatic hydrocarbon derivative had an absorption band beyond 700 nm.

FIG. 13 is a diagram showing fluorescence spectra of the polycyclic aromatic hydrocarbon derivative obtained in Example 3. FIG. 13 shows fluorescence spectra with exciting light having wavelengths of 360 nm to 600 nm. FIG. 13 understandably shows that the resultant polycyclic aromatic hydrocarbon derivative has maximum fluorescence intensity at around a wavelength of 700 nm, with exiting light having wavelengths of 500 nm or more.

The resultant polycyclic aromatic hydrocarbon derivative was measured for its plane-direction dimension and thickness in the same manner as in Example 1, resulting in a plane-direction dimension of 58 nm and an aspect ratio of 160.

Example 4

Also in Example 4, graphene oxide was prepared in the same manner as in Example 1.

With use of the graphene oxide prepared as described above, a polycyclic aromatic hydrocarbon derivative represented by the following formula (5) was synthesized. In the formula (5), i-Bu represents an isobutyl group.

[Chemical 18]

Formula (5)

Specifically, a stir bar was placed in a 50-mL eggplant flask equipped with a three-way cock and they were baked with a heat gun under flowing argon gas. After cooling them, 118.8 mg of the graphene oxide prepared in the same manner as in Example 1 were weighed into the eggplant flask in a dry box. After the weighing, the eggplant flask was taken out from the dry box, 5 mL of oxalyl chloride (manufactured by Sigma-Aldrich Co. LLC.) were added by syringe operation under a flow of argon, and 0.10 mL of dry N,N-dimethylformamide (DMF, manufactured by Sigma-Aldrich Co. LLC.) were further added. Next, the mixed liquid containing graphene oxide, oxalyl chloride, and DMF in the eggplant flask was subjected to an ultrasonic process for 3 hours with an ultrasonic processor (item No. "US-103," manufactured by SND Co., Ltd.). Then, the mixed liquid was subjected to operation of heating with hot water at 60° C. under stirring with a stirrer for 4 days. After the mixed liquid was thus reacted, 5 mL of dry DMF, 5 mL of triethylamine, and 281.8 mg of 3,4-diamino-2,5-ditertiarybutylthiophene were further added to the eggplant flask, and the mixed liquid was further reacted continuously with hot water at 80° C. in an argon atmosphere for 5 days. The resultant reactant was dissolved in ethyl acetate, washed with an aqueous pH 4 solution, and then subjected to separation through a separating funnel with an aqueous saturated NaCl solution to recover an ethyl acetate recovery liquid. The ethyl acetate recovery liquid was dried with mirabilite for 12 hours, and then ethyl acetate was removed with an evaporator and purification was performed through a bio bead column (developing solvent: THF) to give 117.2 mg of a polycyclic aromatic hydrocarbon derivative.

FIG. 14 is a diagram showing a FT-IR spectrum of the polycyclic aromatic hydrocarbon derivative obtained in Example 4. As shown in FIG. 14, it was clarified that the resultant polycyclic aromatic hydrocarbon derivative has a peak derived from the substituent shown in the formula (5) in addition to a peak derived from graphene oxide.

FIG. 15 is a diagram showing a $^1$H-NMR spectrum of the polycyclic aromatic hydrocarbon derivative obtained in Example 4. As shown in FIG. 15, the resultant $^1$H-NMR spectrum was observed to show a signal derived from an i-Bu group at around 1 to 1.5 ppm and a signal derived from an aromatic ring at around 6.5 to 8.0 ppm.

Accordingly, FIGS. 14 and 15 clarified the production of the polycyclic aromatic hydrocarbon derivative represented by the formula (5).

FIG. 16 is a diagram showing an absorption spectrum of the polycyclic aromatic hydrocarbon derivative obtained in Example 4. As shown in FIG. 16, the resultant polycyclic aromatic hydrocarbon derivative had an absorption band beyond 700 nm.

FIG. 17 is a diagram showing fluorescence spectra of the polycyclic aromatic hydrocarbon derivative obtained in Example 4. FIG. 17 shows fluorescence spectra with exciting light having wavelengths of 360 nm to 480 nm. FIG. 17 understandably shows that the resultant polycyclic aromatic hydrocarbon derivative has maximum fluorescence intensity at around a wavelength of 550 nm.

The resultant polycyclic aromatic hydrocarbon derivative was measured for its plane-direction dimension and thickness in the same manner as in Example 1, resulting in a plane-direction dimension of 67 nm and an aspect ratio of 184.

(Evaluation of Electrochromic Properties)

The polycyclic aromatic hydrocarbon derivatives obtained in Examples 1 to 4 were evaluated for their electrochromic properties. First, a light-modulating laminate was prepared as follows using each of the polycyclic aromatic hydrocarbon derivatives obtained in Examples 1 to 4.

The polycyclic aromatic hydrocarbon derivative was added to toluene to give a concentration of 1% by weight. Next, the mixture was subjected to ultrasonic irradiation for 30 minutes to disperse the polycyclic aromatic hydrocarbon derivative in toluene and thus give a dispersion liquid.

Here, two conductive film-attached substrates were prepared that were each obtained by disposing an ITO conductive film on a glass substrate. The dispersion liquid was applied onto one of the conductive film-attached substrates by spin coating. Next, the conductive film-attached substrate was heated at 85° C. for 1 hour to remove toluene and dry the polycyclic aromatic hydrocarbon derivative on the conductive film-attached substrate. These procedures gave a light-modulating film disposed on the conductive film-attached substrate.

Next, a support member was disposed on the light-modulating film. Next, the other of the two conductive film-attached substrates was disposed on the support member. An electrolyte solution (LiPF$_6$ 1 mol/L, solvent EC:DMC=1:2 (volume ratio)) was injected into and sealed in a space surrounded by the light-modulating film, the support member, and the conductive film-attached substrate. The procedures described above gave a light-modulating laminate.

A DC voltage of 3 V was applied to the light-modulating laminate, which was evaluated for a change in light transmittance. Table 1 shows results of the difference (%) in light transmittance particularly at a wavelength of 500 nm and a change in color (visual inspection) before and after the application of the voltage. The change in light transmittance was measured with a spectral device (model No. V-670) manufactured by JASCO Corporation. In Table 1, the mark ○ in the evaluation of the change in color (visual inspection) shows that the light-modulating laminate was transparent before the application of the voltage and changed its color to dark brown after the application of the voltage.

TABLE 1

| | Evaluation of electrochromic properties | |
|---|---|---|
| Structural formula | Difference (%) in Transmittance at wavelength of 500 nm | Change in color (visual inspection) before and after application of voltage |
| Ex. 1 Formula 4 | 39 | ○ |
| Ex. 2 Formula 6 | 25 | ○ |
| Ex. 3 Formula 7 | 28 | ○ |
| Ex. 4 Formula 5 | 43 | ○ |

EXPLANATION OF SYMBOLS

1: Light-modulating laminate

2A, 2B: First and second supports

3A, 3B: First and second conductive films

4A, 4B: First and second conductive film-attached substrates

5: Light-modulating film

6: Electrolyte layer

7: Support member

The invention claimed is:

1. A light-modulating material comprising a polycyclic aromatic hydrocarbon derivative that is a derivative of a polycyclic aromatic hydrocarbon having 6 or more aromatic rings and has a substituent represented by a following formula (3):

[Chemical 3]

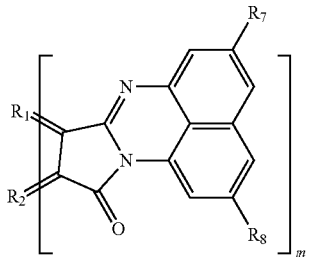

Formula (3)

in which $R_1$ and $R_2$ are carbon atoms of the aromatic rings in the polycyclic aromatic hydrocarbon; $R_7$ and $R_8$ are each a hydrogen atom, an alkyl group having 1 to 20 carbon atoms, an alkoxy group (with an alkyl group having 1 to 20 carbon atoms), a cyano group, a nitro group, an amino group, an acylamino group, an alkylcarbonyl group, an arylcarbonyl group, or an acetoxy group; and m is a number of substituents.

2. A polycyclic aromatic hydrocarbon derivative that is a derivative of a polycyclic aromatic hydrocarbon having 6 or more aromatic rings and has a substituent represented by a following formula (10):

[Chemical 4]

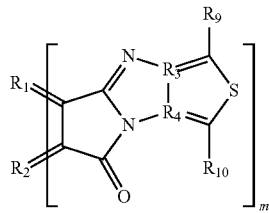

Formula (10)

in which $R_1$ and $R_2$ are carbon atoms of the aromatic rings in the polycyclic aromatic hydrocarbon; $R_3$ and $R_4$ are carbon atoms of an aromatic ring or a heterocyclic ring in a group having the aromatic ring or the heterocyclic ring; $R_9$ and $R_{10}$ are each a hydrogen atom, an alkyl group having 1 to 20 carbon atoms, an alkoxy group (with an alkyl group having 1 to 20 carbon atoms), a cyano group, a nitro group, an amino group, an acylamino group, an alkylcarbonyl group, an arylcarbonyl group, or an acetoxy group; and m is a number of substituents.

3. The light-modulating material according to claim 1, having a plane-direction dimension of 100 nm or less.

* * * * *